United States Patent
Shameli et al.

(10) Patent No.: US 12,042,233 B2
(45) Date of Patent: Jul. 23, 2024

(54) MALLEABLE SUCTION INSTRUMENT WITH OFFSET POSITION SENSOR

(71) Applicant: Acclarent, Inc., Irvine, CA (US)

(72) Inventors: Ehsan Shameli, Irvine, CA (US); Itzhak Fang, Irvine, CA (US); Babak Ebrahimi, Irvine, CA (US); Fatemeh Akbarian, Rancho Palos Verdes, CA (US); Roozbeh Borjian, Irvine, CA (US)

(73) Assignee: ACCLARENT, INC., Irvine, CA (US)

( * ) Notice: Subject to any disclaimer, the term of this patent is extended or adjusted under 35 U.S.C. 154(b) by 719 days.

(21) Appl. No.: 17/239,762

(22) Filed: Apr. 26, 2021

(65) Prior Publication Data
US 2021/0353363 A1 Nov. 18, 2021

Related U.S. Application Data

(60) Provisional application No. 63/023,486, filed on May 12, 2020.

(51) Int. Cl.
*A61M 1/00* (2006.01)
*A61B 34/20* (2016.01)

(52) U.S. Cl.
CPC .............. *A61B 34/20* (2016.02); *A61M 1/71* (2021.05); *A61B 2034/2051* (2016.02); *A61B 2034/2072* (2016.02); *A61M 2207/00* (2013.01)

(58) Field of Classification Search
CPC ... A61B 2017/00738; A61B 2217/005; A61M 1/87; A61M 1/71; A61M 1/774; A61M 1/84
See application file for complete search history.

(56) References Cited

U.S. PATENT DOCUMENTS 6,626,902 B1    9/2003   Kucharczyk et al.
7,670,327 B2    3/2010   Kucharczyk et al.
(Continued)

FOREIGN PATENT DOCUMENTS

DE      202016104966 U1    12/2016
EP           3409219 A1    12/2018
(Continued)

OTHER PUBLICATIONS

International Search Report and Written Opinion dated Jul. 28, 2021, for International Application No. PCT/IB2021/053741, 14 pages.

*Primary Examiner* — Deanna K Hall
(74) *Attorney, Agent, or Firm* — Morgan, Lewis & Bockius LLP

(57) ABSTRACT

An apparatus such as a suction instrument includes a position sensor proximate to a distal tip of a malleable shaft. A sensor wire couples the position sensor to a processor of an image guided surgery system such that signals generated by the position sensor can be interpreted to determine the position of the surgical instrument. The malleable shaft includes a malleable outer shaft and a flexible inner tube. The flexible inner tube includes a primary lumen that can provide suction, fluid, or various deployable surgical tools, and an inner lumen that holds the sensor wire. Protected within the inner lumen, the sensor wire runs the length of the shaft and exits the inner lumen and passes through a slot in the outer shaft to reach the position sensor. A heat shrink cover wraps the distal tip, sealing the components together and providing an opening suitable for suction.

20 Claims, 9 Drawing Sheets

(56) References Cited

U.S. PATENT DOCUMENTS

| | | |
|---|---|---|
| 7,720,521 B2 | 5/2010 | Chang et al. |
| 8,821,376 B2 | 9/2014 | Tolkowsky |
| 10,362,965 B2 | 7/2019 | Kesten et al. |
| 10,463,242 B2 | 11/2019 | Kesten et al. |
| 10,561,370 B2 | 2/2020 | Salazar et al. |
| 2014/0364725 A1 | 12/2014 | Makower |
| 2017/0000984 A1 | 1/2017 | Duindam et al. |
| 2018/0085174 A1 | 3/2018 | Radtke et al. |
| 2018/0344248 A1 | 12/2018 | Zeng et al. |
| 2018/0344978 A1 | 12/2018 | Shameli et al. |
| 2019/0046358 A1 | 2/2019 | Gliner |
| 2020/0107726 A1 | 4/2020 | Salazar et al. |

FOREIGN PATENT DOCUMENTS

| | | | |
|---|---|---|---|
| EP | 3476271 A2 | 5/2019 | |
| WO | WO 2016/183220 A1 | 11/2016 | |

MALLEABLE SUCTION INSTRUMENT WITH OFFSET POSITION SENSOR

PRIORITY

This application claims priority to U.S. Provisional Pat. App. No. 63/023,486, entitled "Malleable Suction Instrument with Offset Position Sensor," filed May 12, 2020, the disclosure of which is incorporated by reference herein, in its entirety.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

The position sensor that allows an instrument position to be detected and displayed during IGS navigation is commonly located at or near the distal tip of a tracked surgical instrument. A sensor wire couples the position sensor to a controller or processor that receives signals indicative of the instrument's position, and interprets those signals in order to provide and display IGS navigation interfaces. Since the sensor wire spans the entire length of the instrument and is relatively small in diameter it is susceptible to damage and resulting signal loss as a result of normal activities (e.g., advancing, rotating, or flexing a shaft of the surgical instrument, deploying tools via catheters or channels, operating drilling or cutting features of the surgical instrument).

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
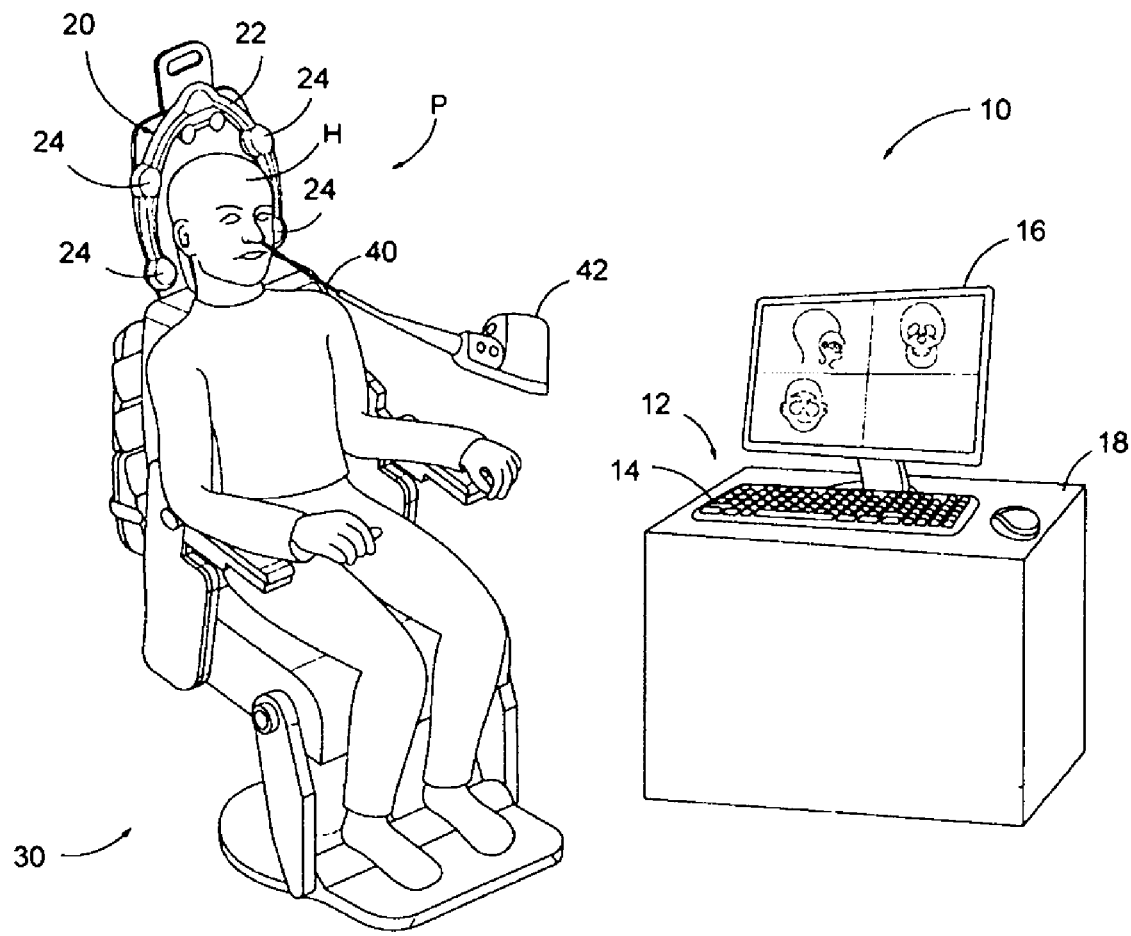
FIG. 1 depicts a schematic view of an exemplary surgery navigation system being used on a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein, in its entirety.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P) to produce a tracked area that the IGS navigation system (10) associates a coordinate system with. A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein, in its entirety.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24), and that generates data usable to determine the position of the sensor within the magnetic fields. A coupling unit (42) is secured to the proximal end of navigation guidewire (40) and is configured to provide communication of data and other signals between console (18) and navigation guidewire (40). Coupling unit (42) may provide wired or wireless communication of data and other signals. While the position sensor is located in guidewire (40) in this example, such a position sensor may be integrated into various other kinds of instruments, such as dilation catheters, guide catheters, guide rails, suction instruments, pointer instruments, registration probes, curettes, patient trackers, and other instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. No. 10,463,242, entitled "Guidewire Navigation for Sinuplasty," issued Nov. 5, 2019, the disclosure of which is incorporated by reference herein, in its entirety. In the event that the operator is also using an endoscope, the endoscopic image may also be provided on display screen (16).

II. Exemplary Suction Instrument with Laterally Offset Position Sensor

Surgical instruments tracked by the IGS navigation system (10) may include a position sensor that reacts to an alternating magnetic field generated by field generator assembly (20) and thereby produces signals indicative of the position of the sensor within the field. Such a position sensor may be in communication with a connected device such as the coupling unit (42) or the processor (12) via one or more sensor wires that run from the sensor itself, along the length of the surgical instrument. In some suction instruments or delivery catheters, the sensor wire may be positioned within a primary channel or on an exterior of the shaft of the instrument, and may couple to the position sensor at the tip of the instrument. In such implementations, there may be a risk that an exterior sensor wire is damaged by another instrument (e.g., a drilling or cutting instrument used in conjunction), or that an interior sensor wire is damaged by instruments passing through the channel (e.g., a stylet used to clear a blockage in a suction instrument, a cutting instrument passing through a delivery catheter).

Figure 2:
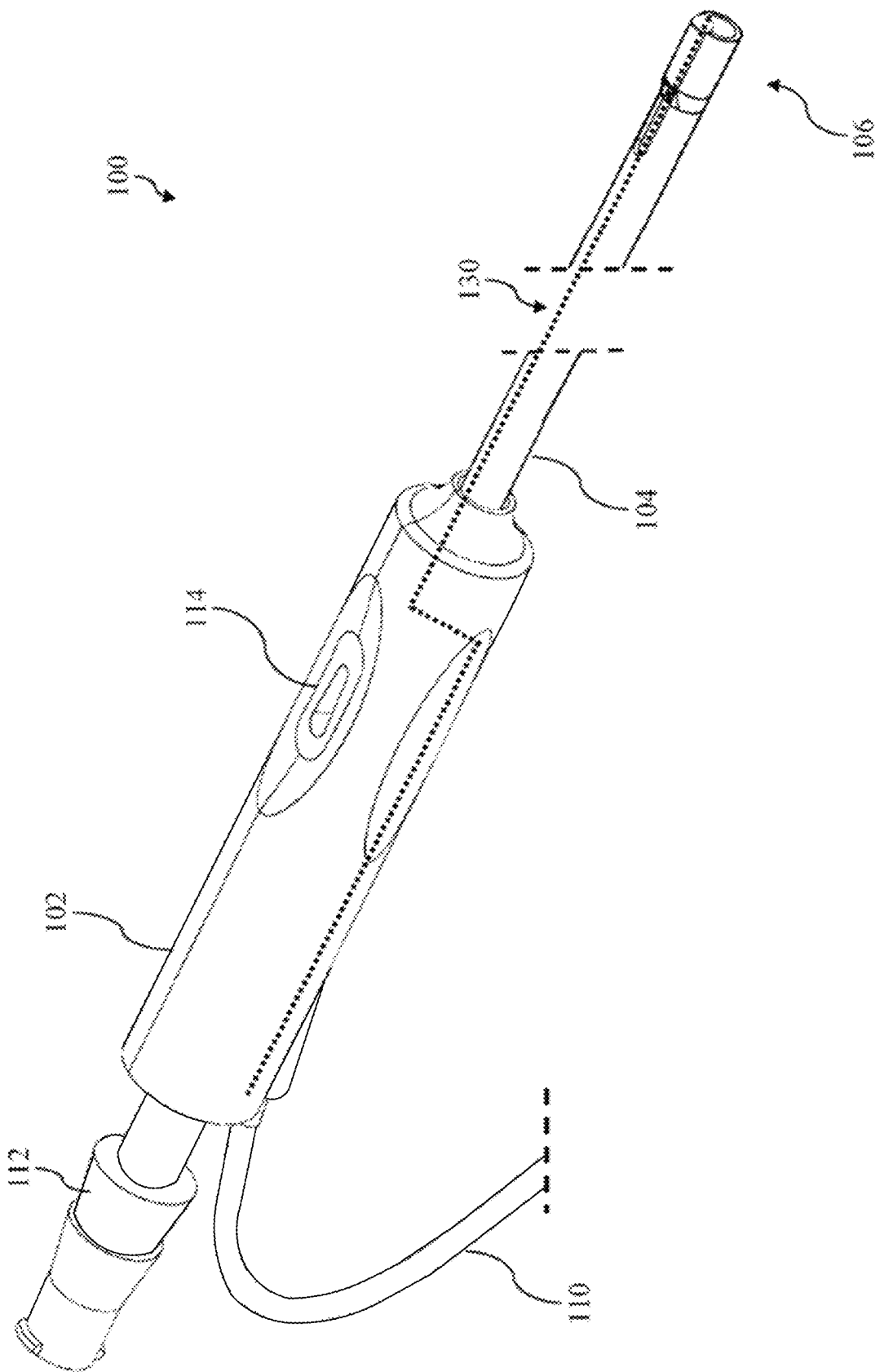
FIG. 2 shows a perspective view of an exemplary suction instrument with the path of an embedded position sensor wire indicated by a dotted line.

To protect the delicate sensor wires during use and prevent loss of instrument tracking due to damaged wires, a surgical instrument may be implemented with a dedicated channel that protects the sensor wire while not compromising normal operation of the instrument. As an example, FIG. 2 shows a perspective view of an exemplary suction instrument (100) with the path of an embedded position sensor wire indicated by a dotted line. The suction instrument (100) includes a grip (102) adapted to be held in the hand during use in a medical procedure, a shaft assembly (104) whose distal end may be inserted into the patient during use, and a tip (106) at the distal end of the shaft assembly (104) from which suction and/or irrigation may be provided when positioned near the surgical site. A hose connector (112) may be coupled to a suction and/or irrigation source via a hose or tube. Hose connector (112) provides access to a suction channel that runs through the shaft assembly (104) and terminates at the distal tip (106). A port (114) is positioned on the grip (102) and opens into the suction channel. When the port (114) is uncovered, suction from the hose connector (112) will draw suction to atmosphere primarily at the port (114) instead of drawing suction at the distal tip (106). When the port (114) is covered, the suction will be communicated to the distal tip (106). In this manner, a user can cover or uncover the port (114) (e.g., such as with a thumb or other finger when holding the grip (102)) in order to selectively apply suction at the surgical site.

A cable (110) holds and protects portions of the sensor wire that are located outside of the suction instrument (100). The sensor wire (130) may be of a diameter much smaller than the cable (110) and may include a flexible rubber coating. After exiting the cable (110), the sensor wire (130) runs along a path within the suction instrument (100) illustrated as a dotted line in FIG. 1. When the suction instrument (100) is in use, it may sometimes be necessary to run a stylet or other blockage cleaning tool through the suction channel via the hose connector (112), the port (114), or the distal tip (106). The shaft assembly (104) may also be shaped or flexed in varying ways in order to traverse anatomical passages and position the distal tip (106) at the surgical site. In both cases, it can be seen that, absent protection, a significant length of the sensor wire (130) may be subject to damage during blockage clearing or shaping.

Figure 3:
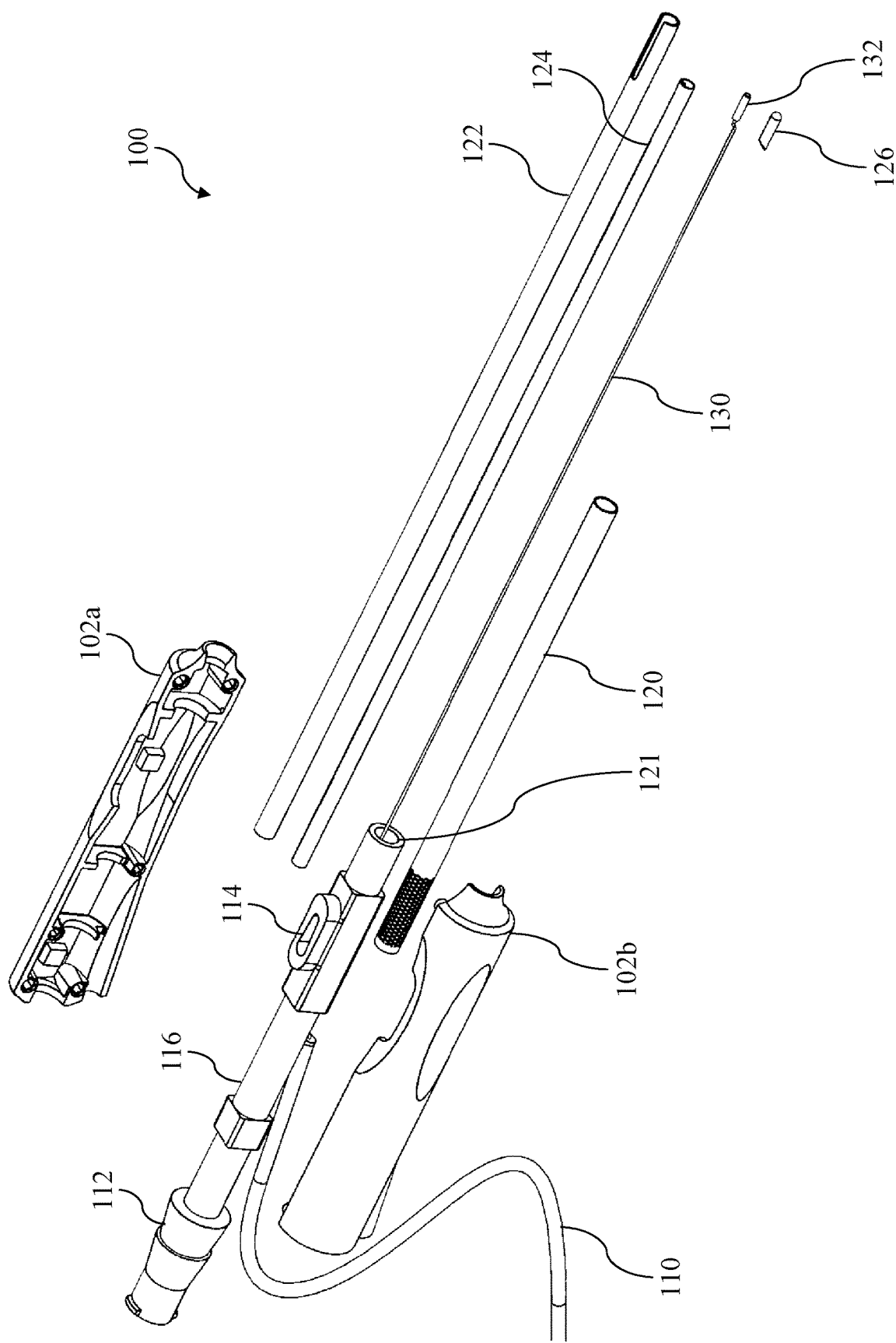
FIG. 3 shows an exploded perspective view of the suction instrument of FIG. 2.

FIG. 3 shows an exploded perspective view of the suction instrument (100). The grip (102) is separated into a first half (102a) and a second half (102b), which are adapted to hold a body (116) whose hollow interior defines the suction channel. The components of the shaft assembly (104) can be seen to include a shaft base (120), an outer shaft (122), and an inner tube (124). The inner tube (124) is of a diameter that allows it to snugly fit inside the outer shaft (122); and of a length similar to the outer shaft (122). The outer shaft (122) is of a diameter that allows it to snugly fit inside the shaft base (120), and the shaft base (120) itself is of a diameter that fits snugly within the distal suction channel opening (121) of the body (116).

The sensor wire (130) can be seen protruding from the suction channel opening (121) and terminating at a position sensor (132) proximate to the distal end of the outer shaft (122). Position sensor (132) may include one or more coils that are configured to generate signals that indicate the location of position sensor (132) within three dimensional space (e.g., within the head (H) of the patient (P)), in response to alternating electromagnetic fields generated by field generators (24), like the position sensor in guidewire (40) as described above. When the suction instrument (100) is fully assembled, the sensor wire (130) is immediately contained within an inner lumen (125) (shown in FIGS. 4, 5A, 5C-7, and 10-11) of the inner tube (124), as will be illustrated in more detail below. The inner lumen (125) may be formed inside the inner tube (124) as part of a manufacturing process (e.g., an extrusion process), or may be a separate piece that is later coupled to the interior of the inner tube (124).

The position sensor (132) is sized to fit within a sensor cover (126), and the sensor cover (126) itself is sized to fit within a slot at the distal end of the outer shaft (122), as will be illustrated in more detail below. The shaft base (120) may be formed of stainless steel (e.g., or another metal), and may be malleable or rigid, depending upon the length of the shaft assembly (104) that is desired to be shapeable. The shaft base (120) makes the proximal side of the shaft assembly (104) stiffer than the distal end to provide steerability of the tool during a surgical procedure. The outer shaft (122) may be formed of a malleable material such as stainless steel, while the inner tube (124) may be formed of a polymer or other flexible material such that it can be shaped by the outer shaft (122). The cover (126) may be formed of a rigid polymer, metal, or other material. Cover (126) may protect the sensor (132) from damage due to navigation or parallel use with other surgical tools (e.g., drills, debriders), while the material (e.g., stainless steel) of the outer shaft (122) protects the sensor wire (130) from the same. By way of example only, inner tube (124) may have a wall thickness of around 0.005 inches, and may be comprised of a flexible material (e.g., Pebax 5333, Tecobax MPD-441-45D) that accommodates bending of the outer shaft (122) by a 0.25 inch or greater bend radius without kinking or otherwise damaging the sensor wire (130).

Figure 4:
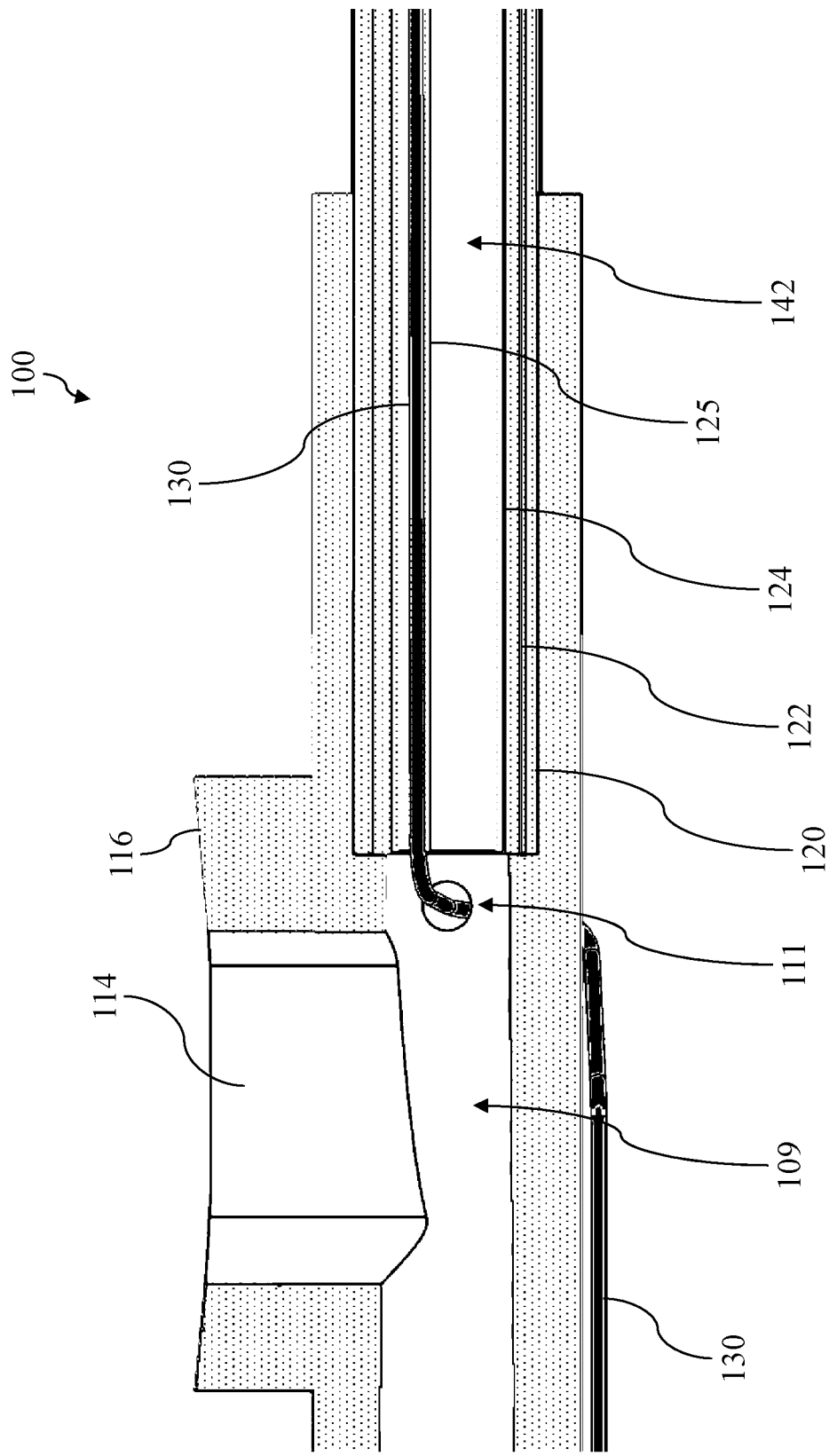
FIG. 4 shows a cross-sectional side view of a body of the suction instrument of FIG. 2.

FIG. 4 shows a cross sectional view of the body (116) of the suction instrument (100). The proximal ends of the shaft base (120), outer shaft (122), and inner tube (124) are visible coaxially nested within each other and within the distal end of the body (116). A portion of the sensor wire (130) can be seen running along the underside of the body (116), outside of the suction channel (109). The sensor wire (130) enters the suction channel (109) through a laterally facing hole (111) formed in the sidewall of the body (116), and immediately enters an inner lumen (125) that runs along an interior wall of the inner tube (124). The hole (111) and the inner lumen (125) may be positioned in order to minimize or completely eliminate any length of the sensor wire (130) that is exposed within the suction channel (109), in order to mitigate risks relating to use of a stylet or other tool to clear the suction channel (109) of blockages. In some implementations, the sensor wire (130) may be loosely positioned within the suction instrument (100), between the body (116) and the grip (102), with a distal end coupled to the position sensor (132) and an overall length that allows for some movement of the sensor wire (130) due to bending or shaping of the outer shaft (122)). This may allow the sensor wire to longitudinally shift or be pulled taught within the inner lumen (125) without breaking as a result of shaping.

Figure 5A:
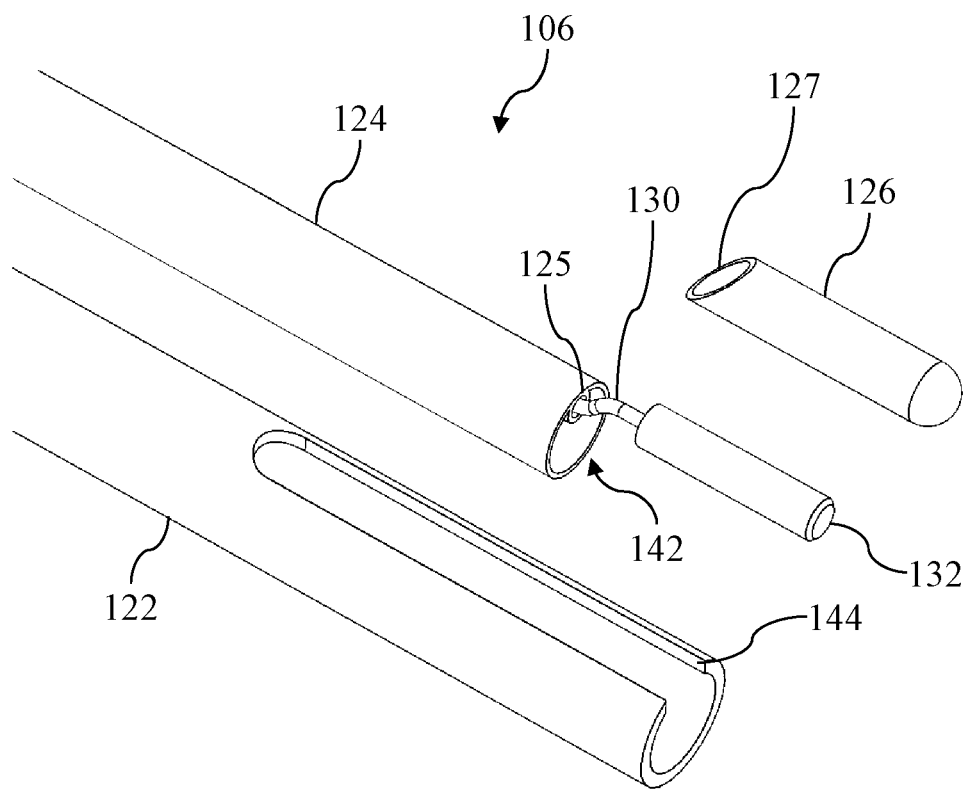
FIG. 5A shows an exploded perspective view of a distal tip of the suction instrument of FIG. 2.

FIG. 5A shows an exploded perspective view of the distal tip (106) of the suction instrument (100). The sensor wire (130) can be seen exiting the distal end of the inner lumen (125) and coupling to the sensor (132). The sensor cover (126) is ball shaped at the distal end to make it a ball tip or ball point suction instrument (100), though other shapes may be used as well. The sensor cover (126) includes an opening sized to receive the sensor (132), which may be loosely fit, friction fit, or fixed within the cover (126) by an adhesive or other coupling element or material. The cover (126) is also sized to fit within a transverse slot (144) in the distal end of the outer shaft (122), as can be seen in the fully assembled distal tip (106) of FIG. 5B. In that figure, the sensor (132)

is contained within the sensor cover (126), and a small portion of the sensor wire (130) can be seen extending from the sensor cover (126) and entering the inner lumen (125). The sensor cover (126) is positioned within the slot (144) just above a distal opening (136) of the outer shaft (122), and substantially or completely fills the distal end of the slot (144) so that the opening (136) is unbroken and capable of delivering focused suction and/or irrigation. The sensor cover (126) has a bevel (127) at the proximal end of sensor cover (126), which may provide a substantially smooth transition at the exterior of shaft assembly (104) while also protecting the inner side of the portion of sensor wire (130) passing through slot (144), as best seen in FIG. 5C.

Figure 5B:
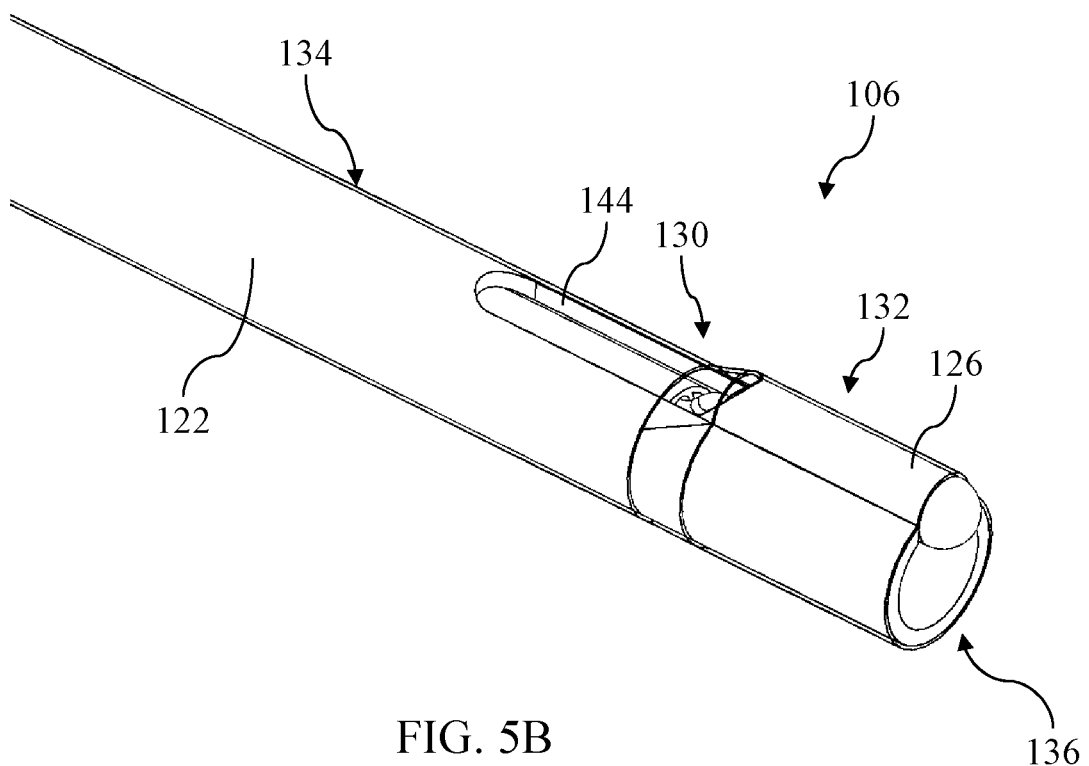
FIG. 5B shows a perspective view the assembled distal tip of FIG. 5A, including a cover seal.
Figure 5C:
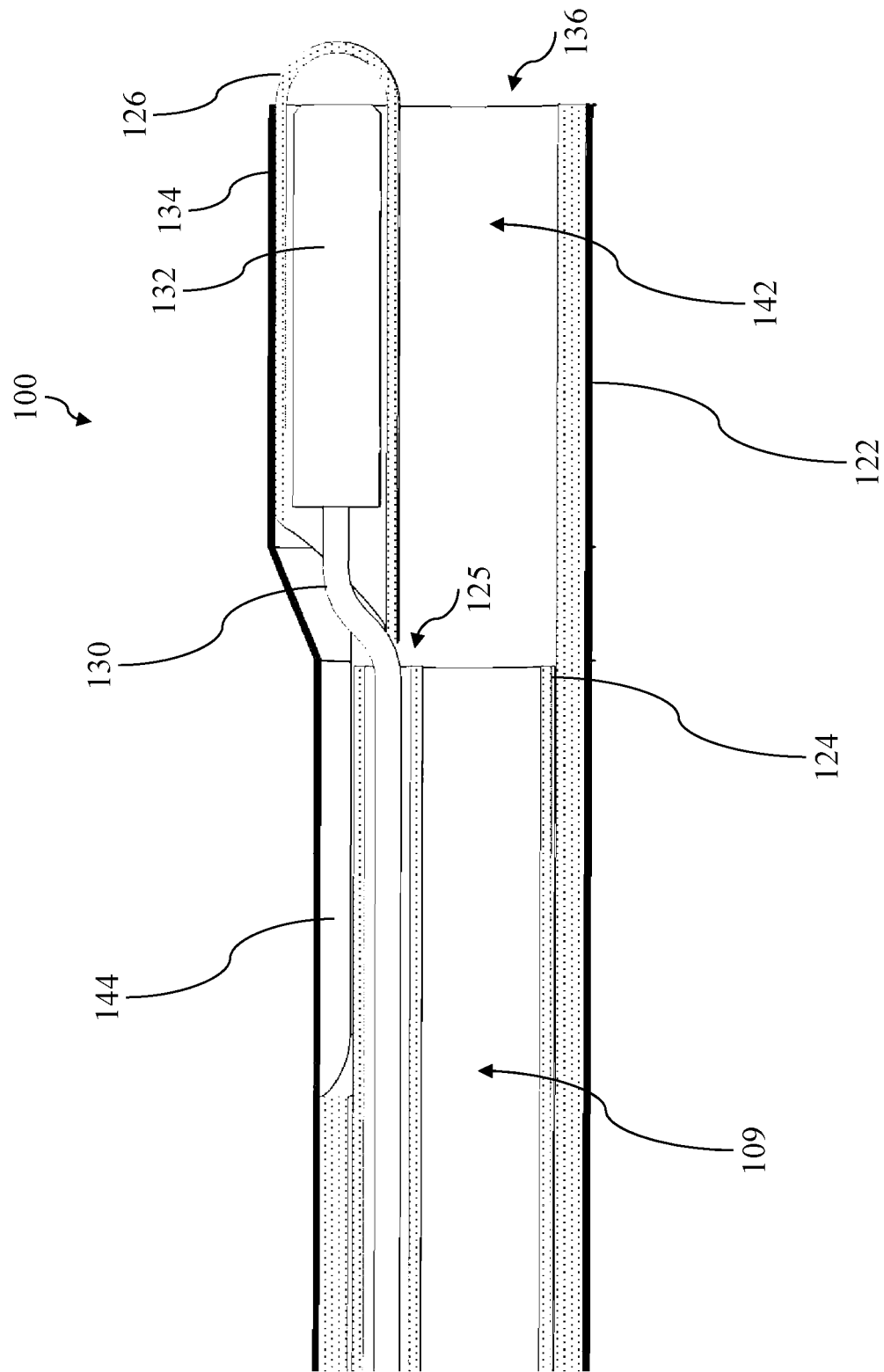
FIG. 5C shows a cross-sectional side view of the distal tip of FIG. 5B.

As shown in FIG. 5C, a cover seal (134) is wrapped around the distal tip (106), and in some implementations may extend along some or all of the remainder of the shaft assembly (104). The cover seal (134) may be, for example, a polymer heat wrap coating that is loosely placed on the distal tip (106) and then heated to cause shrinkage and a tight fit and seal, or may be a sealant or coating that is applied and that dries or cures in order to hold the components of the distal tip (106) in place and seal gaps. The cover seal (134) substantially covers the sensor cover (126) and descends along its bevel (127) to the outer shaft (122), where it entirely covers the slot (144) in order to concentrate suction at the distal opening (136) and prevent suction loss via the slot (144).

FIG. 5C shows a cross-sectional view of the assembled distal tip (106) of FIG. 5B. The cover seal (134) is visible on the exterior edge of the assembly, holding the sensor cover (126) within the slot (144). The edge of the slot (144) may be sized to receive and hold the sensor cover (126) while preventing sensor cover (126) from completely passing through the slot (144), such that application of the cover seal (134) couples the pieces together and prevents shifting. The cover seal (134) extends down the bevel (127) of the sensor cover (126) and covers the entirety of the shaft (144), resulting in a small space between distal opening of the inner lumen (125) and the opening of the sensor cover (126) that the control wire (130) loosely spans, allowing for movement or flexing of the sensor wire (130) as a result of bending of the shaft assembly (104). The inner lumen (125) may be sealed at one or both openings or may be left open. In some implementations, the sensor wire (130) may substantially fill the interior of the inner lumen (125), such that the effects of any suction or irrigation on the inner lumen (125) are negligible. The sensor cover (126) and inner lumen (125) may be sized and shaped to minimize or eliminate any portion of the control wire (130) that is exposed to the suction channel (109), such as is shown in FIG. 5C. As can be seen, a stylet or other channel clearing tool passing through the suction channel (109) in either direction will be diverted from contact with the sensor wire (130) by the edge or underside of the inner lumen (130), or the underside of the sensor cover (126).

Figure 6:
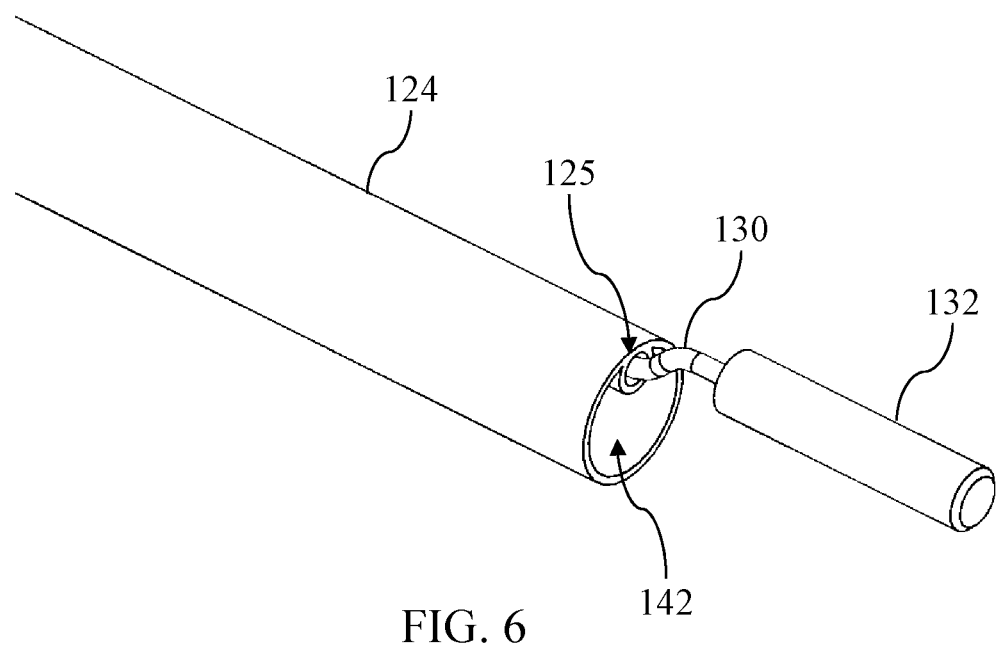
FIG. 6 shows a perspective view of an inner tube of the suction instrument of FIG. 2 with a sensor wire and position sensor extending from an inner lumen.
Figure 7:
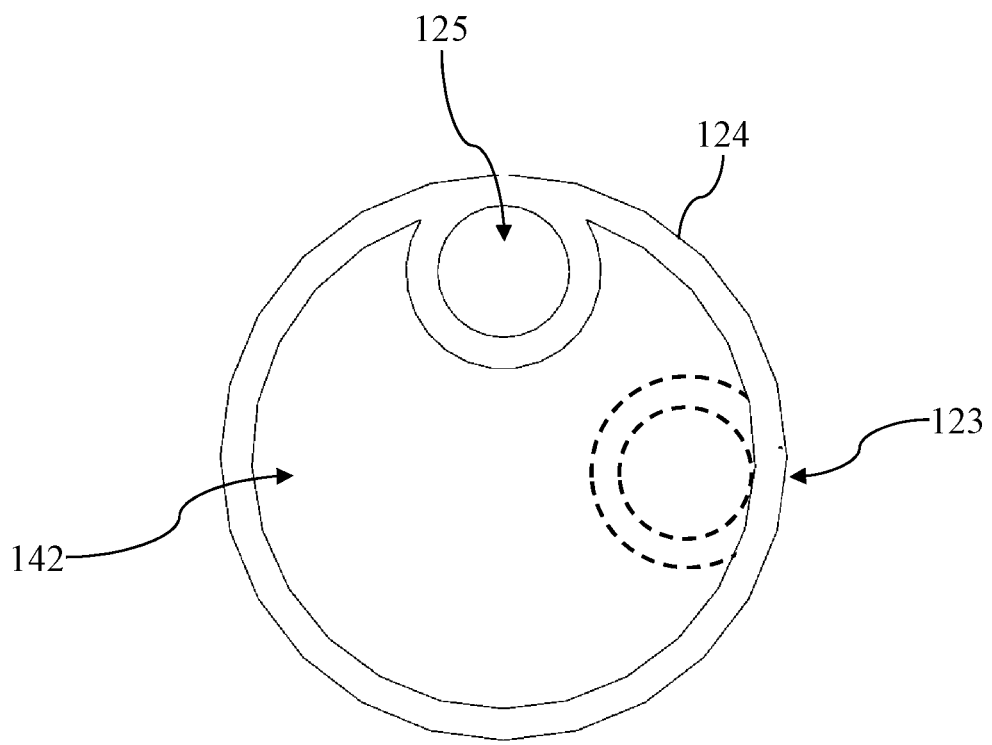
FIG. 7 shows an end view of a distal end of the inner tube of FIG. 6.

FIG. 6 shows a perspective view of the inner tube (124) with the sensor wire (130) extending from the inner lumen (125) and connecting to the position sensor (132). With the outer shaft (122) and sensor cover (126) removed, the inner lumen (125) that holds the sensor wire (130) is visible, as well as the primary lumen (142) that defines the suction channel (109) at the distal tip (106). FIG. 7 shows an elevation view looking down the inner tube (124). The inner lumen (125) is coupled to or formed onto an interior wall of the primary lumen (142), and it can be seen that the majority of the of inner tube's (124) interior is unobstructed to allow for sufficient suction flow.

While the inner tube (124) shown in FIG. 7 and elsewhere shows the inner lumen (125) as being continuously positioned on an upper interior wall of the inner tube (124), some implementations may include an inner lumen that is positioned elsewhere (e.g., on a sidewall or bottom wall), or may include an inner lumen that runs along the interior walls of the inner tube (124) non-linearly so that it twists along the interior of the shaft. As an example, an origin position (123) for the inner lumen (125) is illustrated in FIG. 7. In implementations where the proximal opening of the inner lumen is located as illustrated in FIG. 7, the span of control wire exposed to the suction channel (109) after entering the body (116) would be further minimized (e.g., with reference to FIG. 4, the span of control wire (130) between the hole (111) and the opening of the inner lumen (125) would be further minimized). The rate of twist of the inner lumen (125) position could be selected such that it could be positioned proximate to an opening on the sidewall of the body, and then gradually twist along the shaft until it is just below the slot (144) at the distal tip (106).

Figure 8:
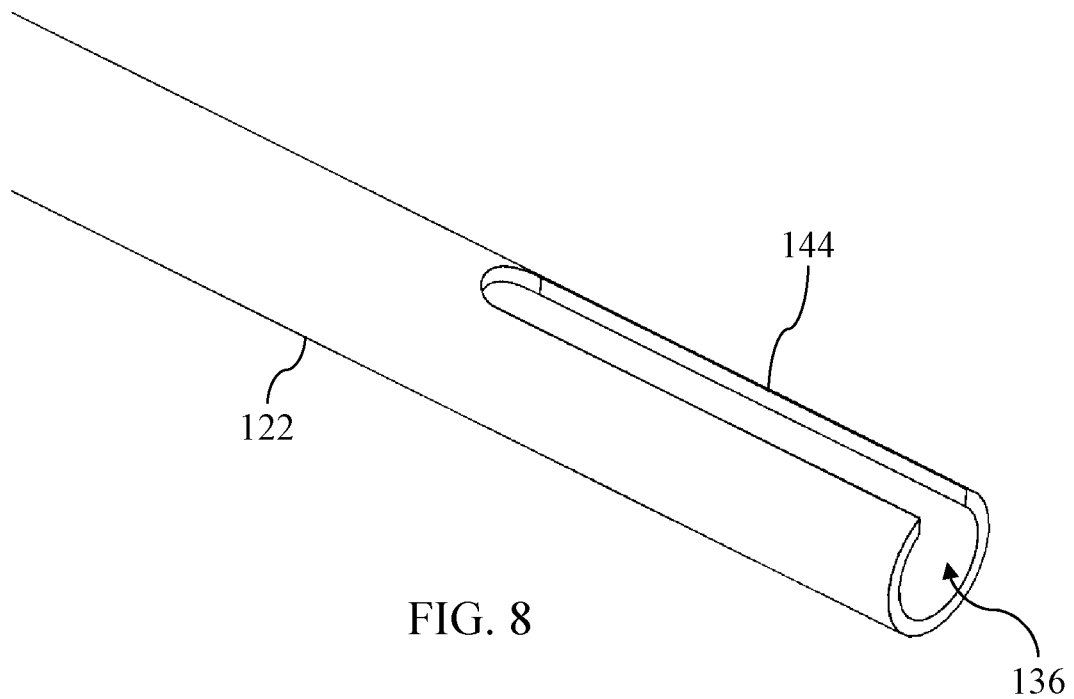
FIG. 8 shows a perspective view of an outer shaft of the suction instrument of FIG. 2 including a slot.
Figure 9:
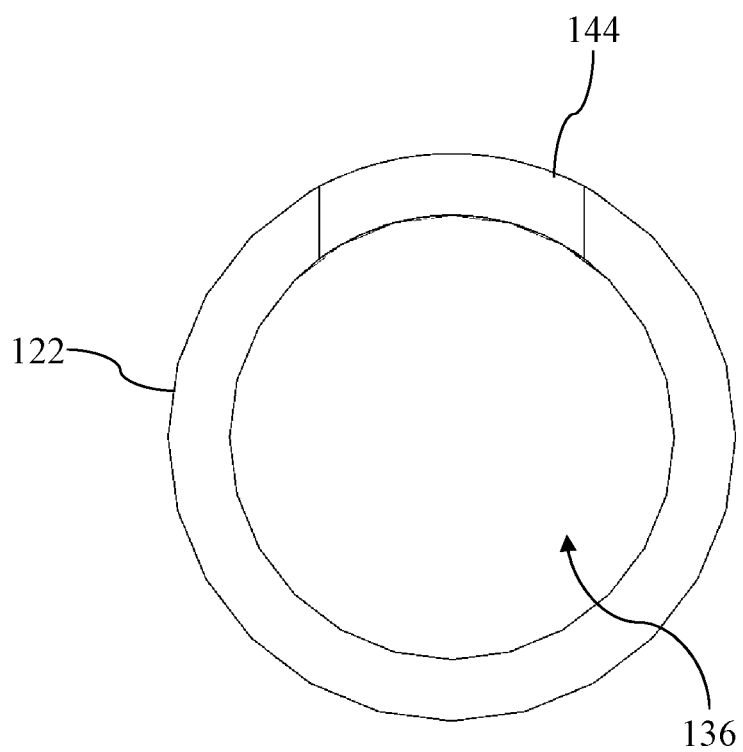
FIG. 9 shows an end view of a distal end of the outer shaft of FIG. 8.

FIG. 8 shows a perspective view of the outer shaft (122) and the slot (144) With the sensor cover (126) removed, the slot (144) can be seen extending from the distal opening (136) and down part of the length of the outer shaft (122) to a distance that allows for the slot (144) to receive the sensor cover (126), and allows for the sensor wire (130) to exit the inner lumen (125) and pass through the slot (144) to enter the sensor cover (126). FIG. 9 shows an elevation view looking down the outer shaft (122). The width of the slot (144) may be such that the full diameter of the sensor cover (126) cannot pass completely through the slot (144), as has been described. In other words, the outer diameter of sensor cover (126) is greater than the width of slot (144).

Figure 10:
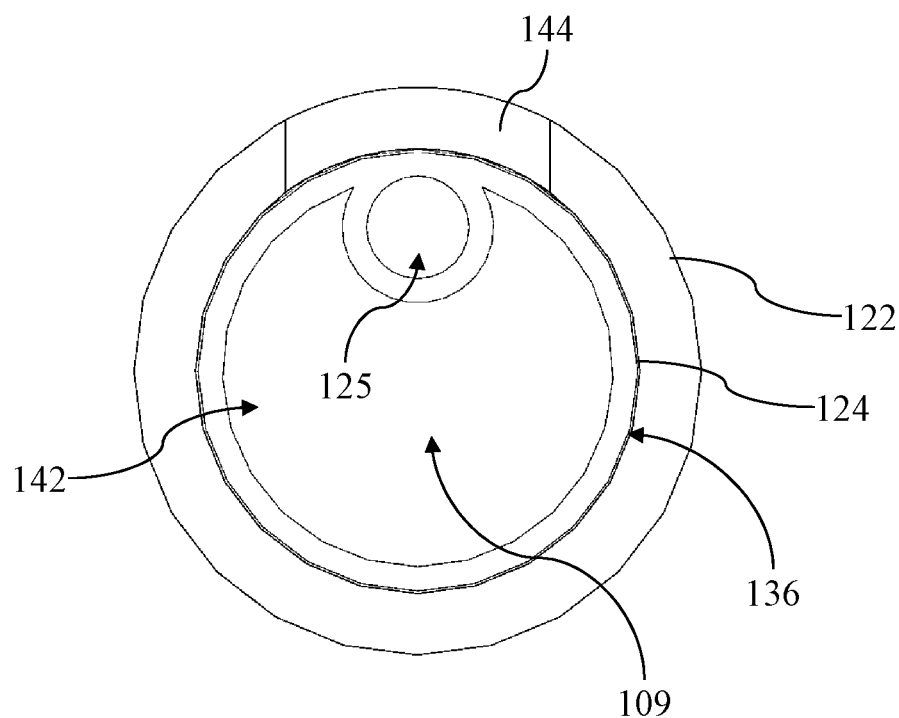
FIG. 10 shows an end view of the inner tube of FIG. 6 inserted within the outer shaft of FIG. 8.
Figure 11:
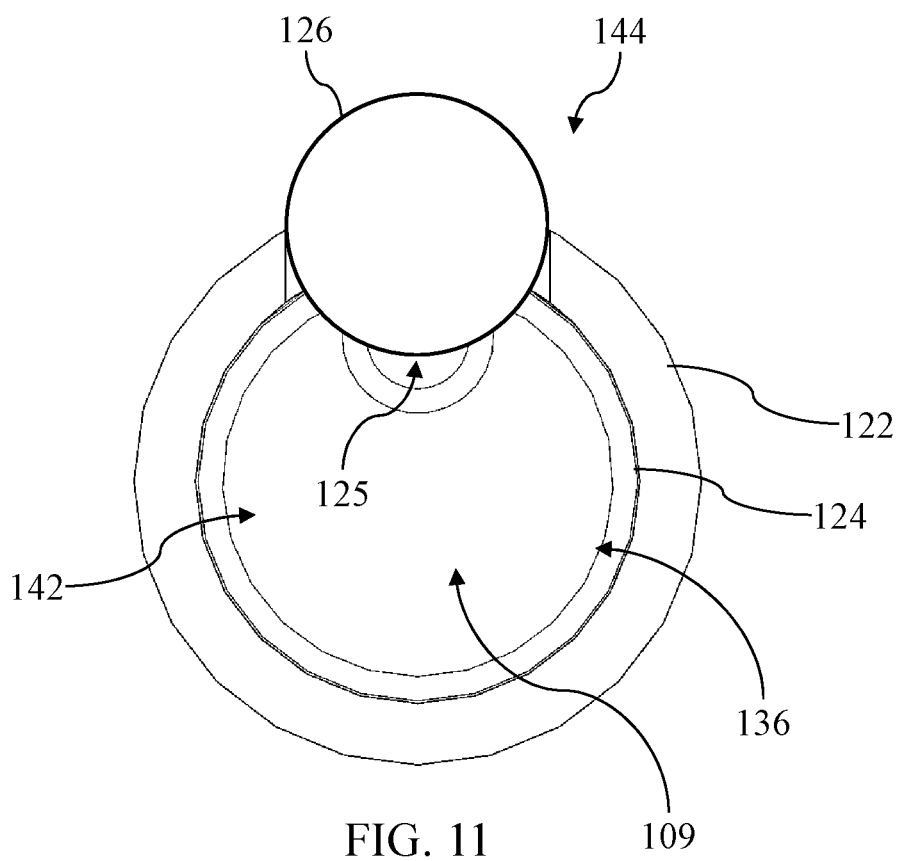
FIG. 11 shows an end view of an assembled distal end of the suction instrument of FIG. 2.

FIG. 10 shows an elevation view looking down the assembled inner tube (124) and outer shaft (122), with the inner lumen (125) aligned with the slot (144) and the primary lumen (142) feeding into the distal opening (136) of the outer shaft (122). FIG. 11 shows an assembled distal tip (106), with the sensor cover (126) installed within the slot (144), and aligned with the inner lumen (125). With the seal cover (134) installed, as shown in FIGS. 5B and 5C, the suction channel within the shaft assembly (104) is unbroken such that the resulting suction is focused at the distal opening (136). Further, it can be seen that with the sensor cover (126) occupying the slot (144), the distal opening (136) itself is unbroken, which allows for strong suction when the distal opening (136) contacts materials or fluids. It should also be appreciated that the sensor cover (126) does not substantially obstruct the primary lumen (142) or the distal opening (136) (e.g., only about 10% or less of the circular area of the distal opening (136) is occupied, while varying implementations may occupy between about 5% and about 25% of the opening).

As also shown in FIGS. 2, 5B-5C, and 11, position sensor (132) is oriented along an axis that is parallel with yet slightly axially offset from the central longitudinal axis of shafts (122, 124). The distance of this lateral offset may be predetermined and fixed. Thus, processor (12) may readily calculate the precise location of distal opening (136) in three-dimensional space based on position-indicative signals that are generated by position sensor (132). Another advantage of the sensor cover (126) being at the distal end of the suction instrument (100) is that it provides a visible reference point for a user of the suction instrument (100). As an example, the sensor cover (126) can be seen to have a convex shape that extends from the slot (144) as a ball point. This ball point shape provides a visible reference point that indicates the location and orientation of the suction instrument (100) when viewed directly or via an endoscope or other camera, or when viewed via an IGS display with a crosshair, illuminated dot, or some other visual indicator overlaid upon the ball point.

While the discussion above has referred to the suction instrument (100) and suction instruments generally as being advantageously implemented with a protected sensor wire, it should be understood that the structures and features disclosed herein may be advantageously implemented in a variety of surgical instruments or other medical instruments that include a shaft and distally mounted position sensor. As an example, instruments such as a catheter (e.g., a fixed, articulated, or malleable catheter) used to guide other instruments to a surgical site, shaver instruments, dilation catheters, and various other kinds of instruments as will be apparent to those skilled in the art in view of the teachings herein may implement a flexible inner lumen that protects the sensor wire without obstructing the delivery channel.

Variations on the systems, methods, and interfaces described above exist and will be apparent to one of ordinary skill in the art in light of this disclosure. For example, while some of the above discussion has described the first point as being the virtual camera's location, it should be understood that in some implementations the first point may be the virtual camera's orientation. This may be advantageous where a clinician has determined a position within the surgical area that is of interest and wishes to select that as the point of orientation (i.e., the second point), then preview a number of camera positions (e.g., the first point) using the real-time virtual endoscopic preview and relational flythrough before making a selection. Choosing the virtual camera's location as the first point may be advantageous where a clinician may use their experience to first determine the best location for the virtual camera, and then may use the real-time virtual endoscopic preview and relational flythrough to choose a point of the surgical area that they would like to focus the virtual camera upon.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly includes: (i) an outer shaft, wherein the outer shaft includes a distal opening and a slot at the distal opening, (ii) an inner tube positioned within the outer shaft, wherein a distal opening of the inner tube is longitudinally offset from the distal opening of the outer shaft and aligned with the slot, and (iii) an inner lumen positioned on an interior wall of the inner tube; (c) a position sensor; (d) a sensor cover that contains the position sensor and is positioned in the slot proximate to a distal opening of the inner lumen; and (d) a sensor wire that is configured to transmit signals from the position sensor, wherein the sensor wire is positioned in the inner lumen and exits the inner lumen via the distal opening of the inner lumen and enters the sensor cover to couple with the position sensor.

Example 2

The apparatus of Example 1, further comprising a shaft cover that encircles the sensor cover and the outer shaft to seal any gaps where the sensor cover meets the outer shaft, and to seal any open portions of the slot.

Example 3

The apparatus of Example 2, wherein the shaft cover comprises a heat wrap cover that is adapted to loosely fit to the sensor cover and the outer shaft and then be tightly sealed by a heat treatment.

Example 4

The apparatus of Example 3, further comprising: (a) a grip that contains the body and at least a portion of the sensor wire that is located outside the body; and (b) a suction connector located at a proximal end of the body and adapted to be coupled to a suction source.

Example 5

The apparatus of any one or more of Examples 1 through 4, wherein the sensor cover: (i) obstructs a majority of the distal opening of the inner lumen, and (ii) obstructs less than about 15% of the circular area of the distal opening of the outer shaft.

Example 6

The apparatus of any one or more of Examples 1 through 5, wherein the sensor wire is configured to translate within the inner lumen while still being coupled with the position sensor.

Example 7

The apparatus of any one or more of Examples 1 through 6, wherein the inner lumen twists along the interior of the inner tube such that: (i) a proximal opening of the inner lumen is positioned on an interior sidewall of the inner tube, and (ii) the distal opening of the inner lumen is positioned on an interior top of the inner tube.

Example 8

The apparatus of any one or more of Examples 1 through 7, wherein the outer shaft is comprised of a malleable material and the inner tube is comprised of a flexible material.

Example 9

The apparatus of Example 8, wherein: (i) the malleable material of the outer shaft comprises a stainless steel, and (ii) the flexible material of the inner tube comprises a polymer.

Example 10

The apparatus of Example 9, wherein the polymer is adapted to allow the inner tube a bend radius of at least 0.25 inches without kinking or breaking.

Example 11

The apparatus of any one or more of Examples 1 through 10, wherein the sensor cover has a diameter, wherein the slot has a width, and wherein the diameter of the sensor cover exceeds the width of the slot such that the sensor cover occupies the full width of the slot.

Example 12

The apparatus of any one or more of Examples 1 through 11, wherein the longitudinal axis of the sensor cover is offset from the longitudinal axis of the inner lumen, and wherein a portion of the sensor wire flexes at an angle to allow the sensor wire to span between the inner lumen and the offset sensor cover.

Example 13

The apparatus of any one or more of Examples 1 through 12, wherein a diameter of the sensor wire substantially occupies a diameter of the inner lumen.

Example 14

The apparatus of any one or more of Examples 1 through 13, wherein the position sensor includes at least one coil configured to generate position data based upon interactions with an alternating magnetic field and transmit the position data via the sensor wire.

Example 15

The apparatus of any one or more of Examples 1 through 14, wherein an opening of the sensor cover is angled such that a proximal edge of the sensor cover extends upwardly from the outer shaft at less than a 90-degree angle.

Example 16

The apparatus of any one or more of Examples 1 through 15, wherein the body comprises a longitudinal channel that terminates at a distal channel opening and the shaft assembly is positioned in the distal channel opening and coupled to the body.

Example 17

The apparatus of any one or more of Examples 1 through 16, wherein the sensor wire: (i) enters the body a hole in the body that is proximate to a proximal opening of the inner lumen, and (ii) enters the inner lumen via the proximal opening of the inner lumen.

Example 18

An apparatus comprising: (a) a shaft assembly that includes: (i) an outer shaft having a distal opening and a slot at the distal opening, (ii) an inner tube positioned within the outer shaft, wherein a distal opening of the inner tube is longitudinally offset from the distal opening of the outer shaft and aligned with the slot, and (iii) an inner lumen positioned on an interior wall of the inner tube; (b) a position sensor; and (c) a sensor wire configured to transmit signals from the position sensor, wherein the sensor wire: (i) is contained within the inner lumen and isolated from the interior of the inner tube, and (ii) exits the inner lumen via a distal opening of the inner lumen, passes through the slot, and couples with the position sensor.

Example 19

The apparatus of Example 18, further comprising a sensor cover that holds the position sensor and is positioned in the slot proximate to the distal opening of the inner lumen.

Example 20

The apparatus of Example 19, further comprising a shaft cover that encircles the sensor cover and the outer shaft to seal any gaps where the sensor cover meets the outer shaft, and to seal any open portions of the slot.

Example 21

The apparatus of any one or more of Examples 18 through 20, wherein the sensor cover: (i) obstructs a majority of the distal opening of the inner lumen, and (ii) obstructs less than about 15% of the circular area of the distal opening of the outer shaft.

Example 22

The apparatus of any one or more of Examples 18 through 21, wherein the inner lumen twists along the interior of the inner tube such that: (i) the proximal opening of the inner lumen is positioned on an interior sidewall of the inner tube, and (ii) the distal opening of the inner lumen is positioned on an interior top of the inner tube.

Example 23

A method for assembling a suction instrument comprising: (a) coupling a shaft assembly with a body, wherein the shaft assembly includes: (i) an outer shaft, wherein the outer shaft includes a distal opening and a lateral slot extending proximally from the distal opening, (ii) an inner tube positioned within the outer shaft, wherein a distal opening of the inner tube is longitudinally offset from the distal opening of the outer shaft, and (iii) an inner lumen positioned on an interior wall of the inner tube; (b) inserting a position sensor into a sensor cover; (c) inserting the sensor cover into the slot, proximate to a distal opening of the inner lumen; and (d) routing a sensor wire through the inner lumen, wherein the sensor wire is coupled with the position sensor and is configured to transmit signals from the position sensor.

Example 24

The method of Example 23, further comprising installing a shaft cover that seals any gaps where the sensor cover meets the outer shaft and that seals any open portions of the slot.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly includes:
      (i) an outer shaft, wherein the outer shaft includes a distal opening and a slot at the distal opening,
      (ii) an inner tube positioned within the outer shaft, wherein a distal opening of the inner tube is longitudinally offset from the distal opening of the outer shaft and aligned with the slot, and
      (iii) an inner lumen positioned on an interior wall of the inner tube;
   (c) a position sensor;
   (d) a sensor cover that contains the position sensor and is positioned in the slot proximate to a distal opening of the inner lumen; and
   (e) a sensor wire that is configured to transmit signals from the position sensor, wherein the sensor wire is positioned in the inner lumen and exits the inner lumen via the distal opening of the inner lumen and enters the sensor cover to couple with the position sensor.

2. The apparatus of claim 1, further comprising a shaft cover that encircles the sensor cover and the outer shaft to seal any gaps where the sensor cover meets the outer shaft, and to seal any open portions of the slot.

3. The apparatus of claim 2, wherein the shaft cover comprises a heat wrap cover that is adapted to loosely fit to the sensor cover and the outer shaft and then be tightly sealed by a heat treatment.

4. The apparatus of claim 1, wherein the sensor cover:
   (i) obstructs a majority of the distal opening of the inner lumen, and
   (ii) obstructs less than about 15% of the circular area of the distal opening of the outer shaft.

5. The apparatus of claim 1, wherein the sensor wire is configured to translate within the inner lumen while still being coupled with the position sensor.

6. The apparatus of claim 1, wherein the inner lumen twists along the interior of the inner tube such that:
   (i) a proximal opening of the inner lumen is positioned on an interior sidewall of the inner tube, and
   (ii) the distal opening of the inner lumen is positioned on an interior top of the inner tube.

7. The apparatus of claim 1, wherein the outer shaft is comprised of a malleable material and the inner tube is comprised of a flexible material.

8. The apparatus of claim 7, wherein:
   (i) the malleable material of the outer shaft comprises a stainless steel, and
   (ii) the flexible material of the inner tube comprises a polymer.

9. The apparatus of claim 1, wherein the sensor cover has a diameter, wherein the slot has a width, and wherein the diameter of the sensor cover exceeds the width of the slot such that the sensor cover occupies the full width of the slot.

10. The apparatus of claim 1, wherein the longitudinal axis of the sensor cover is offset from the longitudinal axis of the inner lumen, and wherein a portion of the sensor wire flexes at an angle to allow the sensor wire to span between the inner lumen and the offset sensor cover.

11. The apparatus of claim 1, wherein a diameter of the sensor wire substantially occupies a diameter of the inner lumen.

12. The apparatus of claim 1, wherein the position sensor includes at least one coil configured to generate position data based upon interactions with an alternating magnetic field and transmit the position data via the sensor wire.

13. The apparatus of claim 1, wherein an opening of the sensor cover is angled such that a proximal edge of the sensor cover extends upwardly from the outer shaft at less than a 90-degree angle.

14. The apparatus of claim 1, wherein the body comprises a longitudinal channel that terminates at a distal channel opening and the shaft assembly is positioned in the distal channel opening and coupled to the body.

15. The apparatus of claim 1, wherein the sensor wire:
   (i) enters the body a hole in the body that is proximate to a proximal opening of the inner lumen, and
   (ii) enters the inner lumen via the proximal opening of the inner lumen.

16. An apparatus comprising:
   (a) a shaft assembly that includes:
      (i) an outer shaft having a distal opening and a slot at the distal opening,
      (ii) an inner tube positioned within the outer shaft, wherein a distal opening of the inner tube is longitudinally offset from the distal opening of the outer shaft and aligned with the slot, and
      (iii) an inner lumen positioned on an interior wall of the inner tube;
   (b) a position sensor; and
   (c) a sensor wire configured to transmit signals from the position sensor, wherein the sensor wire:
      (i) is contained within the inner lumen and isolated from the interior of the inner tube, and
      (ii) exits the inner lumen via a distal opening of the inner lumen, passes through the slot, and couples with the position sensor.

17. The apparatus of claim 16, further comprising a sensor cover that holds the position sensor and is positioned in the slot proximate to the distal opening of the inner lumen.

18. The apparatus of claim 16, wherein the sensor cover:
   (i) obstructs a majority of the distal opening of the inner lumen, and
   (ii) obstructs less than about 15% of the circular area of the distal opening of the outer shaft.

19. The apparatus of claim 16, wherein the inner lumen twists along the interior of the inner tube such that:
   (i) the proximal opening of the inner lumen is positioned on an interior sidewall of the inner tube, and
   (ii) the distal opening of the inner lumen is positioned on an interior top of the inner tube.

20. A method for assembling a suction instrument comprising:
   (a) coupling a shaft assembly with a body, wherein the shaft assembly includes:
      (i) an outer shaft, wherein the outer shaft includes a distal opening and a lateral slot extending proximally from the distal opening,
      (ii) an inner tube positioned within the outer shaft, wherein a distal opening of the inner tube is longitudinally offset from the distal opening of the outer shaft and aligned with the slot, and
      (iii) an inner lumen positioned on an interior wall of the inner tube;
   (b) inserting a position sensor into a sensor cover;
   (c) inserting the sensor cover into the slot, proximate to a distal opening of the inner lumen; and
   (d) routing a sensor wire through the inner lumen, wherein the sensor wire is coupled with the position sensor and is configured to transmit signals from the position sensor.

* * * * *